United States Patent [19]

Colvin et al.

[11] 4,390,741

[45] Jun. 28, 1983

[54] PROCESS FOR THE PURIFICATION OF DIISOPROPENYLBENZENE

[75] Inventors: Howard A. Colvin, Akron; Joel Muse, Jr., Kent, both of Ohio

[73] Assignee: The Goodyear Tire & Rubber Company, Akron, Ohio

[21] Appl. No.: 414,706

[22] Filed: Sep. 3, 1982

[51] Int. Cl.³ .............................................. C07C 7/04
[52] U.S. Cl. .................................... 585/258; 585/266; 585/271; 585/804; 585/807
[58] Field of Search ............... 585/258, 266, 269, 271, 585/273, 804, 807

[56] References Cited

U.S. PATENT DOCUMENTS 3,670,041  6/1972  Juhl et al. ............................ 585/258
4,046,824  9/1977  Ransley .............................. 585/266

FOREIGN PATENT DOCUMENTS 625655   8/1961  Canada ................................ 585/804
1418628  1/1969  Fed. Rep. of Germany ...... 585/804

*Primary Examiner*—Delbert E. Gantz
*Assistant Examiner*—A. Pal
*Attorney, Agent, or Firm*—Alvin T. Rockhill

[57] ABSTRACT

This invention discloses a process for the separation of diisopropenylbenzene from organic impurities in a dehydrogenation mixture comprising: (1) hydrogenating said dehydrogenation mixture to a maximum isopropenylstyrene concentration of no more than about 5% by weight in the presence of a rhodium catalyst and hydrogen to form a hydrogenated dehydrogenation mixture, followed by, (2) fractionally distilling said hydrogenated dehydrogenation mixture under conditions sufficient to separate said diisopropenylbenzene from said organic impurities in said hydrogenated dehydrogenation mixture.

7 Claims, No Drawings

PROCESS FOR THE PURIFICATION OF DIISOPROPENYLBENZENE

BACKGROUND OF THE INVENTION

Diisopropenylbenzene is a monomer that can be used in the preparation of useful polymers and is also a chemical intermediate that can be used in a number of chemical processes. Diisopropenylbenzene can be synthesized by the dehydrogenation of diisopropylbenzene. For example, meta-diisopropylbenzene (m-DIPB) can be dehydrogenated into meta-diisopropenylbenzene (m-DIB) and para-diisopropylbenzene (p-DIPB) can be dehydrogenated into para-diisopropenylbenzene (p-DIB). Unfortunately, in this dehydrogenation process some olefinic impurities are produced as by-products. These olefinic impurities include isopropylstyrene, divinylbenzene, isopropenyl styrene, and other similar organic impurities. Obviously, it would be very desirable to remove these impurities from the meta- or para-diisopropenylbenzene produced by the dehydrogenation of diisopropylbenzene.

It was believed that meta- or para-diisopropenylbenzene could be removed from these organic impurities by fractional distillation. However, when fractional distillations were attempted the contents of the distillation pot (p-DIB or m-DIB and the organic impurities) polymerized into a gel at the elevated temperature needed for the distillation making it impossible. This polymerization even takes place with as much as 1,000 ppm (parts per million) of polymerization inhibitor present in the distillation pot with gel formation long before all of the diisopropenylbenzene can be recovered.

Sometimes unwanted by-products can be removed by hydrogenation. For example, U.S. Pat. Nos. 3,887,632, 3,912,789, and 3,922,318 show that acetylenes can be removed from a stream containing butadiene and/or isoprene by selective hydrogenation.

SUMMARY OF THE INVENTION

It was found that if a dehydrogenation mixture (mixture of diisopropenylbenzene and organic impurities formed in the dehydrogenation of diisopropylbenzene) containing about 3.7% or less by weight isopropenylstyrene (IPS) is heated to the temperature required for fractional distillation (about 150° C. to about 165° C.) that it will not polymerize to a gel in the distillation pot. On the other hand, it was found that if a dehydrogenation mixture containing 7.4% or more by weight isopropenylstyrene is distilled, the contents of the distillation pot polymerizes to a gel in 2 to 5 hours. This is long before all of the diisopropenylbenzene can be recovered. Thus, it was discovered that polymerization and gel formation in the dehydrogenation mixture during distillation can be eliminated by reducing isopropenylstyrene concentrations to below about 3.7 weight percent.

It was unexpectedly found that the isopropenylstyrene in the dehydrogenation mixture could be selectively hydrogenated wihout a significant amount of diisopropenylbenzene being hydrogenated by utilizing a rhodium catalyst. After a dehydrogenation mixture is selectively hydrogenated using a rhodium catalyst to reduce isopropenylstyrene concentrations below 3.7% by weight, it can be fractionally distilled to separate the m-DIB or p-DIB from the organic impurities without gel formation.

This invention discloses a process for the separation of diisopropenylbenzene from organic impurities in a dehydrogenation mixture comprising: (1) hydrogenating said dehydrogenation mixture to a maximum isopropenylstyrene concentration of no more than about 5 percent by weight in the presence of a rhodium catalyst and hydrogen to form a hydrogenated dehydrogenation mixture, followed by, (2) fractionally distilling said hydrogenated dehydrogenation mixture under conditions sufficient to separate said diisopropenylbenzene from said organic impurities in said hydrogenated dehydrogenation mixture. This invention utilizes a process for removing isopropenylstyrene from a dehydrogenation mixture with only minimal hydrogenation of diisopropenylbenzene which comprises: hydrogenating said dehydrogenation mixture in the presence of a rhodium catalyst and hydrogen.

DETAILED DESCRIPTION

Meta-diisopropenylbenzene and para-diisopropenylbenzene can be produced by the dehydrogenation of meta-diisopropylbenzene and para-diisopropylbenzene, respectively. In this diisopropylbenzene dehydrogenation process a dehydrogenation mixture is produced that contains diisopropenylbenzene and a number of organic impurities. These organic impurities include isopropylstyrene, divinylbenzene, isopropenylstyrene, and a number of other olefinic impurities. A small amount of diisopropylbenzene that was not dehydrogenated is usually also present in the dehydrogenation mixture. During the dehydrogenation of meta-diisopropylbenzene as much as 12 percent of the dehydrogenation mixture produced can be isopropenylstyrene which was produced as an unwanted by-product.

In order to fractionally distill the dehydrogenation mixture, to separate the diisopropenylbenzene from organic impurities, the amount of isopropenylstyrene present in the dehydrogenation mixture must be kept below about 5 percent by weight. It is preferable to reduce the amount of isopropenylstyrene (IPS) in a dehydrogenation mixture that will be distilled to about 3.4 weight percent or less.

IPS can be removed from a dehydrogenation mixture by hydrogenation utilizing a rhodium catalyst. The rhodium catalyst that is used in this dehydrogenation reaction can be either supported or unsupported. It is generally preferable for the rhodium to be supported. Some representative examples of supports that can be used for the rhodium include: carbon, aluminum oxide (alumina), barium sulfate, calcium carbonate, and strontium carbonate. A rhodium-on-charcoal catalyst is an excellent choice as the catalyst in this hydrogenation reaction. The catalyst can be in a fixed bed for hydrogenation on a continuous basis or distributed throughout the dehydrogenation mixture in the case of a batch process. This hydrogenation of the dehydrogenation mixture obviously must be conducted in the presence of hydrogen gas.

This hydrogenation reaction can be done in a batch process by distributing the hydrogen gas and rhodium catalyst throughout the dehydrogenation mixture. For example, hydrogen gas can be sparged through the dehydrogenation mixture containing the catalyst while agitating the dehydrogenation mixture to keep the catalyst well dispersed throughout the mixture. This hydrogenation reaction can be run on a continuous bases by introducing hydrogen gas into the zone of the fixed bed catalyst while passing the dehydrogenation mixture through the fixed bed catalyst.

This hydrogenation reaction can be carried out at atmospheric pressure ($1.0 \times 10^5$ Pa) up to about 1000 gauge pounds per square inch ($7.0 \times 10^6$ Pa). It is preferred for the hydrogenation reaction to be run at about 50 gauge pounds per square inch ($4.5 \times 10^5$ Pa) up to about 70 gauge pounds per square inch ($5.8 \times 10^5$ Pa). The hydrogenation reaction for the dehydrogenation mixture containing meta-diisopropenylbenzene can be run at a temperature from about 0° C. up to about 120° C. It is preferable to run this hydrogenation reaction at room temperature (about 20° C. to 24° C.). The hydrogenation reaction for the dehydrogenation mixture containing para-diisopropenylbenzene can be carried out at a temperature from about 50° C. up to about 100° C. It is preferable to run this hydrogenation reaction at about 55° C. to 60° C. This hydrogenation reaction should preferably be continued until about 2 moles of hydrogen are absored for every mole of isopropenylstyrene originally present in the dehydrogenation mixture. More preferably the hydrogenation should be continued until 3 moles of hydrogen are absorbed for every mole of isopropenylstyrene originally present in the dehydrogenation mixture. The hydrogenation of the dehydrogenation mixture results in the formation of a hydrogenated dehydrogenation mixture.

The rhodium catalyst can be removed from a hydrogenated dehydrogenation mixture that was hydrogenated in a batch process by filtration, centrifugation, sedimentation, and the like. If a fixed bed catalyst is used in a continuous hydrogenation process then obviously there is no catalyst that needs to be removed from the hydrogenated dehydrogenation mixture. The m-DIB or p-DIB can be fractionally distilled from a hydrogenated dehydrogenation mixture containing less than about 5 weight percent (preferably 3.4 weight percent or less) isopropenylstyrene using distillation techniques known to those skilled in the art.

DESCRIPTION OF THE PREFERRED EMBODIMENTS

The following examples demonstrate the effectiveness of rhodium catalysts in selectively hydrogenating isopropenylstyrene without significantly hydrogenating diisopropenylbenzene in a dehydrogenation mixture. These examples are merely for the purpose of illustration and are not to be regarded as limiting the scope of the invention or the manner in which it can be practiced. Unless specifically indicated otherwise parts and percentages are given by weight.

EXAMPLE 1

Meta-diisopropylbenzene was dehydrogenated to a crude dehydrogenation mixture that contained the composition shown in Table I. 194 g (grams) of this dehydrogenation mixture was placed into a Parr bottle with 0.6 g of a 5% rhodium-on-charcoal catalyst (50% water weight). The catalyst added contained only 0.015 g of rhodium (50% of the 0.6 g was water weight and 95% of the remaining 0.3 g was carbon). This dehydrogenation mixture was hydrogenated with 50 gauge pounds per square inch ($4.5 \times 10^5$ Pa) of hydrogen gas at room temperature. The composition of the hydrogenated dehydrogenation mixture being produced was determined after 1, 2, and 3 moles of hydrogen per mole of isopropenylstyrene originally present in the dehydrogenation mixture was absorbed. The amounts of the various components given in Table I are given as area percentages as determined by gas chromatography.

TABLE I

| IPS Component | Gas Chromatograph Area Percentages for Various Mixture Components | | | |
|---|---|---|---|---|
| | Moles of $H_2$ absorbed/mole | | | |
| | 0 | 1 | 2 | 3 |
| m-isopropenylethylbenzene | 2.0 | 4.1 | 6.3 | 8.5 |
| m-diisopropylbenzene | 8.7 | 9.1 | 9.2 | 9.8 |
| m-isopropenylstyrene | 7.5 | 5.4 | 2.8 | 0.3 |
| m-isopropenylisopropylbenzene | 16.5 | 16.1 | 15.8 | 16.1 |
| m-diisopropenylbenzene | 39.8 | 38.6 | 39.0 | 37.8 |

As can be determined from Table I, after 2 moles of hydrogen per mole of IPS had been absorbed 63 percent of the m-IPS was removed (hydrogenated) while only 2 percent of the m-DIB was removed. After 3 moles of hydrogen per mole of IPS had been absorbed 96% of the m-IPS was removed while only 5% of the m-DIB was removed. This example illustrates the fact that rhodium is an excellent catalyst for the selective hydrogenation of IPS that hydrogenates only a minimal amount of DIB.

EXAMPLE 2

The same procedure that was employed in Example 1 was used in Example 2 except that palladium was substituted for the rhodium. After 2 moles of hydrogen per mole of IPS was absorbed 46% of the m-IPS had been removed and 13% of the DIB had been removed. After 3 moles of hydrogen per mole of IPS was absorbed 73% of the IPS had been removed and 19% of the DIB had been removed. This Example illustrates the fact that palladium is not as good as rhodium for the selective hydrogenation of IPS in a dehydrogenation mixture (compare Examples 1 and 2).

EXAMPLE 3

100 g of a dehydrogenation mixture containing 87.1% p-DIB, 6.9% p-IPS, and 6% unknown impurities; 220 cubic centimeters of isopropanol; and 0.7 g of a 5% rhodium-on-charcoal catalyst (50% water weight) was placed in a Parr bottle. This mixture was heated to 55° C. at which point all of the solids dissolved. Hydrogen gas was introduced to the bottle at a pressure of $4.5 \times 10^5$ Pa(Pascal) and the mixture was allowed to hydrogenate at 55° C. to 60° C. until 3 moles of hydrogen had been absorbed per mole of IPS originally present in the dehydrogenation mixture. The catalyst was filtered from the hydrogenated dehydrogenation mixture and the mixture was allowed to cool and crystallize. 51.13 g of material was recovered which had a composition of 98.9% p-DIB, 0.5% p-ethylisopropenylbenzene, 0.2% p-isopropenylisopropylbenzene, and 0.4% unknown impurities.

While certain representative embodiments and details have been shown for the purpose of illustrating the invention, it will be apparent to those skilled in this art that various changes and modifications may be made therein without departing from the scope of the invention.

We claim:

1. A process for the separation of diisopropenylbenzene from organic impurities in a dehydrogenation mixture comprising: (1) hydrogenating said dehydrogenation mixture to a maximum isopropenylstyrene concentration of no more than about 5 percent by weight in the presence of a rhodium catalyst and hydrogen to form a hydrogenated dehydrogenation mixture, followed by, (2) fractionally distilling said hydrogenated dehydrogenation mixture under conditions sufficient to separate said diisopropylbenzene from said organic impurities in said hydrogenated dehydrogenation mixture.

2. A process for removing isopropenylstyrene from a dehydrogenation mixture with only minimal hydrogenation of diisopropenylbenzene which comprises: hydrogenating said dehydrogenation mixture in the presence of a rhdoium catalyst and hydrogen.

3. A process as specified in claim 1 wherein said maximum isopropenylstyrene concentration is about 3.4 weight percent or less.

4. A process as specified in claim 1 or 2 wherein said diisopropenylbenzene is meta-diisopropenylbenzene.

5. A process as specified in claim 1 or 2 wherein said diisopropenylbenzene is para-diisopropenylbenzene.

6. A process as specified in claim 4 wherein said dehydrogenation mixture is hydrogenated at a temperature from about 0° C. up to about 120° C. and a pressure of about $1.0 \times 10^5$ Pa up to about $7.0 \times 10^6$ Pa.

7. A process as specified in claim 5 wherein said dehydrogenation mixture is hydrogenated at a temperature from about 50° C. up to about 100° C. and a pressure of about $1.0 \times 10^5$ Pa up to about $7.0 \times 10^6$ Pa.

* * * * *